United States Patent [19]

Pratt et al.

[11] 4,303,538

[45] Dec. 1, 1981

[54] GREASE COMPOSITIONS AND OXYALUMINUM ACYLATE INTERMEDIATE COMPOSITIONS USEFUL IN THE PREPARATION THEREOF

[75] Inventors: Charles E. Pratt, Signal Mountain; Charles S. Colburn, Jr., Lookout Mtn., both of Tenn.

[73] Assignee: Chattem, Inc., Chattanooga, Tenn.

[21] Appl. No.: 201,273

[22] Filed: Nov. 4, 1980

[51] Int. Cl.³ .................... C10M 5/14; C10M 7/20; C07F 5/06
[52] U.S. Cl. .............................. 252/37.7; 260/448 R; 260/448 AD
[58] Field of Search ................. 252/37.7; 260/448 R, 260/448 AD

[56] References Cited

U.S. PATENT DOCUMENTS

| | | | |
|---|---|---|---|
| 2,768,138 | 10/1956 | Hotten et al. | 252/35 |
| 3,054,816 | 9/1962 | Rinse | 260/448 |
| 3,345,291 | 10/1967 | Koundakjian et al. | 252/37.7 |
| 3,591,505 | 7/1971 | Polishcek | 252/35 |
| 3,776,846 | 12/1973 | Bailey et al. | 252/37.7 |
| 3,791,972 | 2/1974 | Myers | 252/37.7 |
| 4,132,658 | 1/1979 | Coleman et al. | 252/37.7 |

FOREIGN PATENT DOCUMENTS 825878 12/1959 United Kingdom ................. 252/35

*Primary Examiner*—Delbert E. Gantz
*Assistant Examiner*—Irving Vaughn
*Attorney, Agent, or Firm*—Hill, Van Santen, Steadman, Chiara & Simpson

[57] ABSTRACT

Mixed aromatic/aliphatic oxyaluminum acylates wherein the ratio of the number of aromatic radicals to the number of aliphatic radicals ranges from 3:1 to 19:1 and a process for making such compounds. Also premix compositions useful in grease manufacture are provided along with methods for preparing new greases therefrom.

25 Claims, No Drawings

GREASE COMPOSITIONS AND OXYALUMINUM ACYLATE INTERMEDIATE COMPOSITIONS USEFUL IN THE PREPARATION THEREOF

BACKGROUND OF THE INVENTION

In the art of making aluminum complex greases, two methods of preparation are commonly employed. In one of these methods, an aluminum alkoxide is dissolved in oil stock and two mole equivalents of an acid or acid mixture is added thereto. During subsequent heating, reaction occurred releasing one mole of alcohol per mole of acid introduced. Thereafter, to the resulting system water is added which reacts with the final remaining alkoxy group, thereby releasing the third and final mole of alcohol and producing a hydroxyl group on the aluminum atom. The alcohol produced is removed by distillation, and, since the water is typically added in excess, the excess water is likewise removed by distillation. A typical aluminum alkoxide employed in this method is aluminum isopropoxide; see, for example U.S. Pat. No. 3,345,291 issued to Chevron Research Corporation.

In the second technique, a cyclic aluminum isopropoxide (or other alkoxide) trimer is introduced into a mineral oil. To this mixture is added a carboxylic acid mixture which is appoximately equal to two moles of acid per mole of aluminum. When this mixture is heated, reaction occurs which releases one mole of alcohol per mole of aluminum; see, for example, Rinse U.S. Pat. No. 3,054,816. Apparently, it is possible to reverse the order of addition so that the cyclic aluminum isopropoxide trimer is added after the acids are introduced into the petroleum oil; see, for example, column 4 of Bailey et al U.S. Pat. No. 3,776,846. The alcohol thus produced as a by-product is removed by distillation.

Recently, one of us discovered a class of oxyaluminum acylates which can be used in combination with organic acids to prepare commercially greases of mineral oils in such a way as to avoid the problems of removing alcohol produced as a by-product in the grease manufacture and to avoid the addition and/or removal of water present in a system; see Pratt U.S. Ser. No. 096,933. In Rinse U.S. Pat. No. 3,054,816 (see column 3, lines 53–57), it is suggested that a cyclic aluminum oxide stearate trimer can be mixed with mineral oil and then reacted with benzoic acid at elevated temperature to produce a grease. This suggestion of Rinse, so far as is known, has never been commercially exploited. Moreover, the properties of the grease made by the Rinse procedure are not equivalent to the properties of greases made by using oxyaluminum acylates wherein the ratio of the number of aromatic radicals to aliphatic radicals of the cyclic trimer compound range higher than about 3:1.

In Harson British Pat. No. 825,878 cyclic organoaluminum trimers and linear organoaluminum polymers are used in greases. Thus, mixed benzoate/stearate oxylauminum acylate trimers are shown (see page 4, lines 100–110, Example 3, and Example 17 of Harson), as greases made with cyclic trimers (see Examples 25 and 28). Harson used only low amounts of benzoic acids in his organoaluminum compounds (not more than 35 mole percent) and he experienced difficulty in making smooth greases without lumping. In Example 28 thereof for example, when benzoic acid is present in the "external acids", certain other acids (such as branched chain and short chain acids or dimer acids or unsaturated acids or hydrogenated castor fatty acids must be present. Also, presolution of benzoic acid is needed therein to get a smooth grease. Harson never utilized oxyaluminum acylates wherein the ratio of number of aromatic radicals to aliphatic radicals of the cyclic trimer compounds was higher than about 3:1.

The previous above-referenced oxyaluminum acylates of Pratt (see U.S. Ser. No. 096,933) which contain up to 75 mole percent of aromatic carboxylic acid were mainly prepared by utilizing three carboxylic acids: An aromatic acid, an aliphatic acid, and a lower alkanoic acid. The lower alkanoic acid, during the synthetic preparation procedure, produces, as explained in U.S. Ser. No. 096,933, an ester by-product which is easily volatilized and removed. However, oxyaluminum acylates containing more than about 75 mole percent of aromatic carboxylic acid were found to be generally inoperative for use in the manufacture of aluminum complex greases when made by the three acid route.

Now it has been discovered that new oxyaluminum acylates containing more than about 75 mole percent of an aromatic carboxylic acid, but less than about 95 mole percent of aromatic acid, can be prepared, and, further, that such new oxyaluminum acylates can be used to make aluminum complex greases of seemingly excellent quality. The general compound preparation method employed to make such new oxyaluminum acylates was previously discovered by one of us and is readily applicable for the making of such compounds. The greases made from such new oxyaluminum acylates are produced without the use of water and without the production of water or alcohol as by-products.

The compound preparation method employed to make such new oxyaluminum acylates utilizes only two carboxylic acids for reaction with a starting aluminum alkoxide, and the product new oxyaluminum acylates so made are characteristically clear, homgeneous, relatively low melting materials which are substantially soluble in the organic liquids used to make greases. In contrast, when these same new oxyaluminum acylates are synthesized by the three acid route, the product acylates are not clear, but are heterogeneous in composition, and are not substantially soluble in such organic liquids. Furthermore, greases made with such product acylates are not uniform and characteristically contain opaque solid particles. It is now theorized (but there is no intent to be bound herein by theory) that the three acid route results in the production of product oxyaluminum acylates which contain lower alkanoate substituents which cause such undesirable properties for grease making purposes when one is dealing with oxyaluminum acylates containing more that about 75 mole percent of aromatic carboxylic acid.

By such evidence and reasoning, it is concluded that an oxyaluminum acylate containing more than 75 mole percent aromatic carboxylic acid which is to be used in complex aluminum grease manufacture should preferably not contain any substantial quantity of oxyaluminum acylate wherein the acylate substituents are derived from a lower alkanoic acid (such as acetic acid), in order to make a product grease of uniform, homgeneous texture. Such lower alkanoic acid containing oxyaluminum acylates are high melting products which are theorized to be difficultly dispersable in the liquids normally used to make greases which in turn makes good greases very difficult if not impossible to prepare therefrom.

An all-aromatic oxyaluminum acylate is known to the prior art. Thus, Rinse in U.S. Pat. No. 2,913,468 discloses, in Example 4 thereof, preparation of a compound which can be considered to be identified as oxyaluminum benzoate, allegedly made by the method sometimes termed by those skilled in the art as the controlled hydrolysis method.

In the laboratory, an endeavor was undertaken to make by these teachings of Rinse in such '468 patent oxyaluminum benzoate, and it was also undertaken to prepare oxyaluminum benzoate by the route herein used to make the novel mixed aromatic/aliphatic oxyaluminum acylates of the present invention. By each such route, there was prepared a product which was heterogeneous, not clear to transmitted light, and relatively high melting. Also, each product, so far as is now known, is not appreciably soluble in liquid hydrocarbons of the type conventionally used to make greases.

Laboratory work in connection with the utilization of oxyaluminum acylates in aluminum complex greases seems clearly to indicate that higher quality greases are made when a substantially homogeneous oxyaluminum acylate is employed, an homogeneous oxyaluminum acylate being preparable routinely from mixed aromatic and aliphatic carboxylic acids as provided in the present invention. The presence of even a relatively very small amount of an aliphatic carboxylic acid containing Type (A) radicals (as hereinbelow identified) appears to very substantially enhance the homogeneity and the low melting character of a product oxyaluminum acylate as well as the solubility thereof in liquid hydrocarbons of the type conventionally used to make greases. When, however, an oxyaluminum acylate is heterogeneous, it appears that a product grease which is clear in texture is difficult to obtain.

A further consideration in this invention is the circumstance that it appears, for reasons not now understood, that an aluminum alkoxide does not react to molar completion with a single species of aromatic acid, such as benzoic acid, so that inherently such a reaction system tends to produce a non-uniform reaction product which itself is not, it is theorized, desirable for use in making aluminum complex greases.

Therefore, all-aromatic oxyaluminum acylates are not believed to be suitable for use in the manufacture of aluminum complex greases.

BRIEF SUMMARY OF THE INVENTION

In one aspect, the present invention is directed to a class of new and very useful mixed aromatic/aliphatic oxyaluminum acylates. These acylates may be represented either by the formula:

or by the formula:

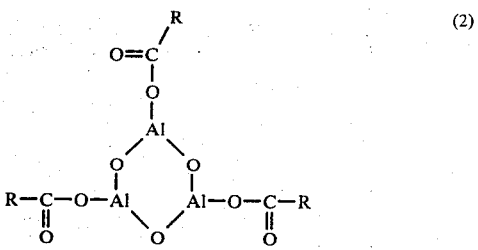

wherein R is selected from the group of radicals consisting of Type (A) radicals and Type (B) radicals where:
  Type (A) radicals: consist essentially of aliphatic radicals each containing from 15 to 38 carbon atoms, and
  Type (B) radicals: consist essentially of aromatic radicals each containing from 6 to 16 carbon atoms.

Also, in any given group of such Formula (1) and/or Formula (2) compounds, the ratio of the number of radicals of said Type (B) radicals to said Type (A) radicals ranges from 3:1 to 19:1 (or the mole percent of said Type (B) radicals ranges from 75 to 95% while the mole percent of said Type (A) radicals correspondingly ranges from about 25 to 5, on a 100 mole percent basis).

A process for making compounds of Formulas (1) and (2) is provided.

In another aspect, the present invention relates to premix compositions for use in grease manufacture which compositions comprise on a 100 weight percent total weight basis:
  (a) from about 30 to 70 weight percent of at least one group of compounds of this invention as defined above, and, correspondingly
  (b) from about 70 to 30 weight percent of an inert organic liquid which itself has a viscosity at 100° F. ranging from about 35 to 50,000 SUS.

Any suitable liquid which is compatible with conventional grease systems, such as a synthetic oil, or an ester of the type conventionally used or known to be compatible with synthetic lubricating oil systems, can be used, if desired, for example.

In such a composition, the above indicated component (a) is uniformly dispersed in the above indicated component (b). As used herein, the term "dispersed", "dispersion", or the like is inclusive of both solutions and suspensions. Preferably, such a composition of this invention has the component (a) substantially completely dissolved in the component (b). This aspect further provides methods for the preparation of such compositions. It is noted that the terms "Component (a)" and "Component (b)" used herein are different from the terms "Type (A) radicals" and "Type (B) radicals" and should not be confused with each other.

In another aspect, this invention relates to an improved process for making a grease. This process involves the step of converting compounds of this invention as above defined in Formulas (1) and/or (2) which are dispersed (preferably dissolved) in an oil (preferably a petroleum derived hydrocarbon oil) by reaction with a carboxylic acid material into an hydroxyaluminum diacyl soap directly without the production of by-product alcohol and without water being present. The following chemical equations are illustrative of this addition reaction whereby no by-products are formed:

Equation I where the compounds of this invention are represented by Formula (1):

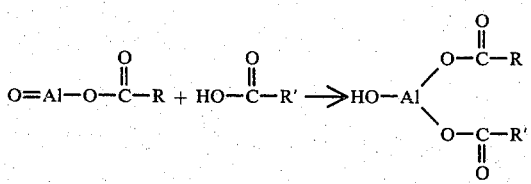

Equation II where the compounds of this invention are represented by Formula (2):

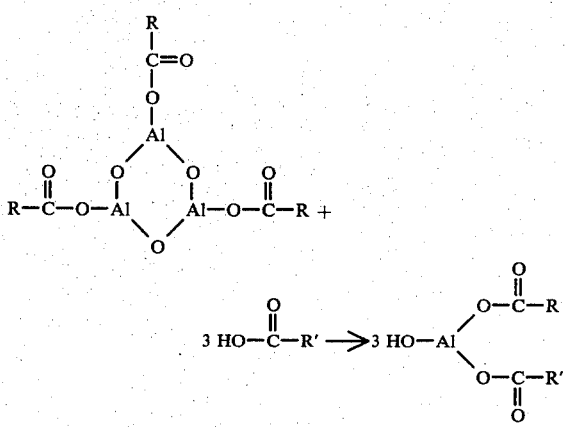

In such equations I and II, and below, R is as above defined, and R' is a radical supplied from among the usual carboxylic acids added by grease manufacturers practicing this process. For example, R' can preferably be the same as R except that the ratio, in any given instance, of Type (B) radicals to said Type (A) radicals can range from 0 to about 5:1. For example, by one presently preferred procedure of this invention, this process involves the steps of heating a mixture of a group of compounds of this invention as above defined in Formulas (1) and (2) with a petroleum derived hydrocarbon having a viscosity at 100° F. ranging from about 35 to 50,000 SUS (though higher and lower viscosity oils may be used if desired) until substantially completely dissolved in such petroleum oil. Next, to such resulting solution is added at least one carboxylic material selected from the group consisting of aliphatic carboxylic acids, aromatic carboxylic acids and mixtures thereof, as more particularly hereinbelow defined. Thereafter, the temperature of the resulting system is raised and maintained at some elevated temperature until at least some of the compounds of this invention present in the system are converted to hydroxyaluminum diacylate soap through reaction with the acids added thereto. In another aspect of this invention, the carboxylic acids can be added to the lubricating oil base first and then the compounds of this invention added to the resulting system.

Finally, in another aspect, this invention relates to improved greases produced by such grease making process of the present invention. In making such an improved grease, the carboxylic acids can be added to the starting oil base first and then the compound(s) of this invention added to this resulting system, or otherwise, if desired.

A principle feature of the present invention is the creation of smooth, clear greases in a simple and reliable manner. No special pains are needed to predissolve the benzoic acid (e.g. aromatic acid) used with the compounds of this invention as above defined in formulas (1) and (2) and no special sequential addition and treating is needed. Both the aromatic acid (e.g. benzoic acid) and the aliphatic acid (e.g. fatty external acids) can be added simultaneously as a solid powder mixture, if desired, a smooth, clear grease is characteristically obtained.

Another principle feature of the present invention is that such mixed aromatic oxyaluminum acylates (as defined hereinabove) permit one to prepare a grease having excellent and controllable high viscosity characteristics compared to the prior art (see, for example, Rinse U.S. Pat. No. 3,054,816).

Another feature of the present invention is that such aluminum acylates (as defined hereinabove) permit one to prepare a grease without the use of added water and without the production of any by-product alcohol whatsoever. The freedom from by-product alcohol formation is highly desirable both from an environmental standpoint and also from a process operation standpoint.

The grease products of this invention characteristically incorporate an aluminum complex soap which, as those skilled in the art appreciate, has reference to a mixture of aluminum soap molecules containing at least one hydroxyl anion for each aluminum cation and substantially two carboxylic acid anions per aluminum atom. By this invention, such an aluminum complex soap has two dissimilar acid anions, such as one aromatic (e.g. benzoate anion) and one saturated aliphatic (e.g. arachidate, stearate, or like fatty carboxylic acid anion). Such an aluminum complex soap is produced by chemical reaction with the mixed oxyaluminum acylates of this invention when the same are used to make a grease in accordance with teachings of the present invention. Specifically, such an aluminum complex soap is generated in situ in a mineral oil continuous phase during the practice of the grease making process of this invention through reaction with carboxylic acid material, but unlike the in situ process of U.S. Pat. No. 3,345,291, no by-product alcohol is produced.

Characteristically, a controllable and uniform thickening of a starting petroleum composition is achieved by the practice of the process of the present invention using the mixed oxyaluminum acylates of this invention.

Other further objects, aims, purposes, features, advantages, uses and the like will be apparent to those skilled in the art from the present disclosure.

DETAILED DESCRIPTION

As those skilled in the art will appreciate, oxyaluminum acylates of which the mixed oxyaluminum acylates of this invention, as defined above in Formulas (1) and (2) are examples, are believed presently to exist either in a monomeric form or in a cyclic trimeric form. The conditions under which one form exists as opposed to the other form are at this time completely unknown.

One class of preferred compounds of this invention are those wherein the Type (B) radicals are derived from benzoic acid. Another class of preferred compounds of this invention are those wherein the Type (A) radicals are derived from stearic acid or isostearic acid and wherein the Type (B) radicals are derived from benzoic acid.

One class of preferred aliphatic carboxylic acids for this invention comprises acids derived from fish oil which contains at least about 50 percent by weight of hydrogenated fatty acids of arachidic and behenic acids, such as "Hydrofol 2022-55", available from the Ashland Chemical Company of Columbus, Ohio, U.S.A.

Any convenient method of making the mixed oxyaluminum acylates of Formulas (1) and/or (2) may be employed including the controlled hydrolysis method where approximately one mole of total acids and approximately one mole of water are reacted with approximately one mole of an aluminum lower alkoxide. The following equations represent the reaction:

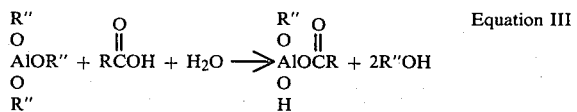

Equation III

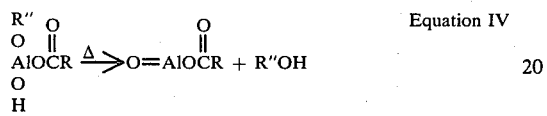

Equation IV

Equations III and IV show the reactions of preparing compounds represented by Formula (1). As those skilled in the art will appreciate, similar equations showing the preparation of compounds represented by Formula (2) can be developed by starting with three moles aluminum lower alkoxide, three moles of acid and three moles of water.

A preferred preparation procedure involves the reactions represented by the following equations:

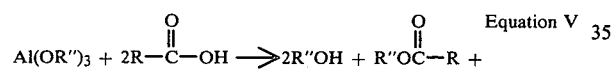

Equation V

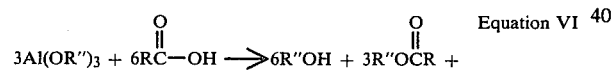

Equation VI

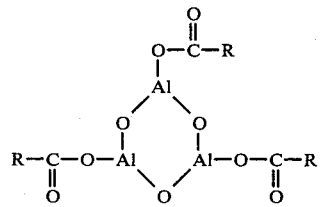

In the above equations: R is as above defined; R″ is a lower alkyl radical. Equation V shows the reaction of preparing compounds represented by Formula (1) and Equation VI shows the reaction of preparing compounds represented by Formula (2).

The desired number ratio of aliphatic radicals to aromatic radicals is achieved by controlling the composition of RCOOH in Equation V and/or VI.

One presently preferred method of preparation involves a two step procedure. Thus, in a first step, two moles of carboxylic acid are combined with one mole of an aluminum trialkoxide (e.g. from about 65° to 150° C.) and reacted at an elevated temperature to form an aluminum alkoxy diacylate and two moles of an alcohol by-product (which continuously distilled off) as illustrated by the following equation:

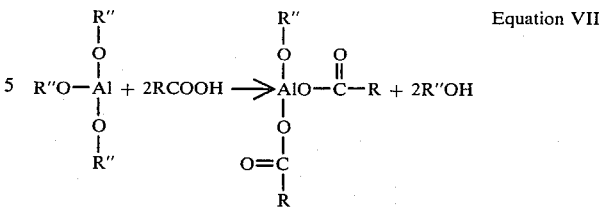

Equation VII

Then, in second step, the product aluminum alkoxy diacylate is thermally decomposed conveniently at atmospheric pressures using, for example, a temperature of from about 150° to 250° C. The thermal decomposition results in a splitting off of a by-product ester composed of the remaining (—OR″) group and one of the acylate groups, as illustrated by the following equation wherein compounds Formula (1) are formed:

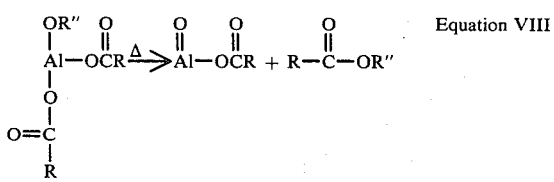

Equation VIII

When making a mixed oxyaluminum acylate of the present invention, a convenient method to use as a starting carboxylic acid mixture, is a mixture of the two acids which will supply the desired radicals for the said mixed oxylauminum acylate. When, for example, an oxyaluminum benzoate/stearate of the type disclosed by the present invention is desired, the acid mixture would be conveniently comprised of benzoic acid and stearic acid. In the above case, the ester formed by the reaction would be a mixture comprised of benzoate and stearate esters. These esters or a portion of them can be removed by vacuum distillation or can be left with the oxylauminum acylate as a carrier fluid. See the copending application filed on even date herewith.

The reaction sequence used to make a compound of this invention (see Equation V and/or Equation VI) can be carried out in organic liquid phase or in some cases it can be carried out as a mass reaction ("neat"). Particularly, when it is desired to use the product mixed oxyaluminum acylate in grease making (as herein described and illustrated), it is preferred, but not necessary, to conduct the synthesis in a mineral oil or ester of the type which approximates that which it is anticipated will be used subsequently for an actual grease making operation. Then, the product as synthesized can be used directly for grease making without further preparative procedures.

However, where for example, it is desired to make such a mixed oxylauminum acylate of Formula (1) and/or (2) in a purified or concentrated form, then the synthesis reaction(s) can be conducted in some cases without solvent or in a relatively low boiling organic inert (as respects reaction products) solvent. Afterwards (if conducted in a solvent) this solvent can be removed by vacuum distillation peferably at reduced pressures to leave a purified, concentrated product. When, for example, such a concentrated product comprised of a compound of this invention is to be used for viscosity regulation of a liquid curable polyester resin system in a vinyl monomer, such as styrene, such concentrated product can be dissolved in such styrene and the resulting solution then added to the polyester resin in a desired amount.

In the present composition above described, presently preferred such liquids for such a premix composition include a petroleum derived hydrocarbon, a phthalate ester, esters produced as by-products in the making of oxyaluminum acylates of this invention, and mixtures thereof.

By the "inert organic" in reference to "liquid" reference is had to the circumstance that such liquid is itself not reactive with oxyaluminum acylates under the conditions of manufacture and use described herein.

Any convenient method may be employed to make an intermediate grease making composition of this invention. One presently preferred method, for example, involves, as a first step, admixing of at least one aluminum trialkoxide with a mineral oil which has a viscosity at 100° F. of from about 35 to 50,000 SUS and which has dispersed therein from about 30 to 72 weight percent of a carboxylic acid mixture based upon the total combined weight of such compounds and said mineral oil. Aluminum trisopropoxide is presently preferred because of its availability and the relatively low boiling point of its alcohol and esters; however, other alkoxides may be used such as aluminum tri sec butoxide, and the like. The total amount of such aluminum tri alkoxide so admixed is equal to about one mole aluminum alkoxide per two moles of acid.

Next, one heats the resulting system to a temperature where alcohol derived from such lower alkoxide groups begins to distill off. Heating is continued until two moles of the alcohol are distilled off on a theoretical basis.

Then one further heats such system to a temperature where the alkoxy aluminum diacylate decomposes to form an oxyaluminum acylate and a mixture of lower alkyl esters of the starting acids. The mole ratio of oxyaluminum acylate to total esters is 1:1 on a theoretical basis.

In the carboxylic acid mixture, the molar ratio of aromatic to aliphatic (higher alkanoate) radicals, controls the molar ratio of aromatic radicals to aliphatic radicals in the oxyaluminum acylates of the present invention, from about 15 to 38 carbon atoms, and, correspondingly, each aromatic carboxylic acid molecule of which contains from about 6 to 16 carbon atoms.

To make a grease of this invention using a mixed oxyaluminum acylate of Formula (1) and/or (2), for example, one employs a mineral starting oil having a viscosity at 100° F. of from about 35 to 50,000 SUS. In such oil, at least one carboxylic acid material is contacted with such mixed oxyaluminum acylate with preferably both reactant types being dispersed (more preferably dissolved) in the oil. Such contacting carried out at a temperature sufficient to produce reaction between said carboxylic acid material and said oxyaluminum acylate compound, and such contacting is continued until at least some of such oxyaluminum acylate compound has been converted into an aluminum soap. The product aluminum soap is an hydroxy aluminum diacylate. The resulting grease containing such hydroxy aluminum diacylate is then milled and packaged. It can be milled at room temperatures or at any elevated temperatures up to about 200° C. with temperatures below about 150° C. being presently preferred.

In one presently preferred grease making grease process of the present invention, the following steps are employed:

First, one heats mixture of petroleum derived hydrocarbon oil having a viscosity of 100° F. of from about 35 to 50,000 SUS and a grease making composition as above described. This mixture contains a total amount of aluminum in the range from about 0.01 to 2.0 weight percent based on total mixture weight. Such heating is conducted at temperatures, and for times, sufficient to substantially completely dissolve or uniformly disperse all starting mixed oxyaluminum acylates present in said hydrocarbon oil.

Next, one admixes with the resultant such mixture of Step One a total of from about 0.8 to 1.2 moles (per mole of oxyaluminum acylate present in said resultant such mixture) of at least one carboxylic acid material selected from the group consisting of aliphatic monocarboxylic acids containing from 15 through 40 carbon atoms each and aromatic monocarboxylic acids containing from 6 through 16 carbon atoms each, Finally, one heats and gradually raises the temperatures of the product mixture, all the while agitating such product mixture, until at least some of such starting mixed oxyaluminum acylates present in the first step have been converted into hydroxy aluminum diacylate (aluminum soap) by reaction in situ with said carboxylic acid material.

As indicated, in such grease making process of this invention, the starting mixed oxyaluminum acylates of Formula (1) and/or Formula (2) present in a base oil are reacted at least partially (preferably substantially completely) with carboxylic acid materials. A starting such mixed oxyaluminum acylate provides from a stoichiometric standpoint approximately one-half of the acylate radicals needed to produce an aluminum soap which is formed from the reaction of such mixed oxyaluminum acylate with carboxylic acid material, such aluminum soap being a compound which contain approximately two acyl groups and one hydroxyl group each group being directly bonded to an aluminum atom (one name for such soap being hydroxy aluminum diacylate).

In calculating the molar quantity of carboxylic acid material to be used (added) for reaction with a mixed oxyaluminum acylate in making a grease according to this invention (based on the number of carboxyl groups present in the carboxyl acid material), it is sometimes convenient to use a mole ratio ranging from about 0.8 to 1.2 of total quantity of carboxylic acid material to total quantity of mixed oxyaluminum acylate.

In a grease prepared by the teachings of this invention, such an aluminum soap is preferably characterized by having the total number of acyl radicals of any given soap molecule composed of a ratio of aliphatic acyl groups to aromatic acyl groups ranging from about 1.3:0.7 to 0.7:1.3. Presently preferred aliphatic acyl groups are derived from fatty carboxylic acids each mixture having an aliphatic containing group of at least about 16 carbon atoms. Also, presently preferred aromatic acyl groups are derived from benzoic acid.

In a grease prepared by the teachings of this invention, it is not necessary to have all of the starting mixed oxyaluminum acylate compounds converted to such an aluminum soap, although for reasons of obtaining a maximum thickening of a given base oil based upon a given quantity of mixed oxyaluminum acylate in admixture therewith, it is presently preferred to achieve a substantially complete conversion of starting mixed oxyaluminum acylate compounds into aluminum soap. However, partial conversion is sometimes preferred as when, in a given grease manufacturing situation, excess mixed oxyaluminum acylate beyond a theoretical or calculated quantity of mixed oxyaluminum acylate is added to a starting reaction system so as to permit processing flexibility. For example, with such an excess quantity, in solution in an oil, one can add only sufficient carboxylic acid material as is necessary to achieve some predetermined system viscosity at some predetermined processing temperature, such a system viscosity having previously been determined to be characteristic of a given grease viscosity desired at ambient temperatures, according to the wishes of a given grease maker in some given instance. Such a grease could be used as a "master batch" (that is, more oil and acid could subsequently be added thereto).

Although in making a grease in accordance with this invention, it is presently preferred to use, as the starting organo aluminum compound which is convertible into aluminum soap by reaction with caboxylic acid materials, only a mixed oxyaluminum acylate as defined above in Formulas (1) and/or (2) (because of the circumstance that no by-product alcohol is produced in converting this compound to an aluminum soap), nevertheless, as those skilled in the art will appreciate, such mixed oxyaluminum acylates may be used, if desired, in combination with other such starting organoaluminum compounds known to the prior art of grease making by forming aluminum soaps. For example, a grease maker may desire to use up stocks on hand of such prior art organoaluminum compounds gradually, or he may desire to use the compounds of this invention in combination with such prior art materials as aluminum stearate for reasons of economy or for other reasons.

In general, when such a starting organoaluminum compound mixture is used, it is preferred to employ a mixture wherein at least about 50 weight percent thereof, on a total mixture weight basis, is comprised of mixed oxyaluminum acylate as defined above in formulas (1) and/or (2).

In its reaction with mixed oxyaluminum acylates, the hydroxyl group of a carboxyl moiety may be visualized as automatically going to the aluminum of the starting mixed oxyaluminum acylate as the soap is being formed.

In addition to, or in admixture with, petroleum derived (mineral) grease making base oils, suitable specialized starting oils adapted for use in the grease making process of the present invention include lubricating oils of naphthenic base, paraffinic base hydrocarbons, mixed base mineral oils, vegetable oils, synthetic oils, including synthesized hydrocarbon base fluids, alkylene polymers, polysiloxanes, ester-type oils such as dicarboxylic acid ester type oils, liquid esters of phosphorous acids, such as are shown in U.S. Pat. No. 2,768,138), and the like. In general, preferred starting base oils have viscosities at 100° F. ranging from about 35 to 50,000 SUS, but other inert organic liquids can be used with viscosities outside of the range.

To make a grease using compounds of Formula (1) and/or (2) in an oil, a grease maker need use no particular type of carboxylic acid material for reaction therewith. For example, it now appears that the teachings of the prior art with respect to the use of various carboxylic acids, combinations thereof, order of contacting, temperature conditions, and the like in connection with the use of the prior art aluminum alkoxides in grease making can be employed to make greases from compounds of Formula (1) and/or (2), except that here no by-product alcohol is produced and no water is needed. Mono and dicarboxylic acids can be used, as can halo substituted such acids like chloroacetic acid dichloroacetic acid, and the like. Examples of suitable dicarboxylic acids include succinic. One particularly preferred monocarboxylic acid is presently isostearic because such acid which is branched $C_{18}$ saturated acid, is a relatively low viscosity liquid at ambient conditions and tends to bring down the melting point and softening point of derivatives thereof, including especially aluminum soaps thereof. For examples of U.S. patent teachings of extremely wide variability in types of acids that can be added to an oil for reaction with the mixed oxyaluminum acylates of this invention to make an aluminum soap, as desired in grease making, see U.S. Pat. No. 3,476,684 (involving mono and dichloro acetic acids), or U.S. Pat. No. 3,413,222 (involving succinic acid). Dimer acids, such as dimerized vegetable oil carboxylic acids, such as are offered commercially by Emery Industries, can also be used as the carboxylic acid material.

A presently preferred class of compounds within the scope of Formulas (1) and/or (2) comprises such compounds wherein the number ratio of such Type (B) radicals to such Type (A) radicals ranges from about 3:1 to 19:1. In such class, the Type (B) radicals are preferably derived from benzoic acid. Such preferred compounds are relatively easy for a grease maker to convert into a grease in the presence for example, of a hydrocarbon oil. Such compounds containing a higher ratio of benzoic acids to aliphatic acids than is disclosed in the prior art presently appear to be particularly desirable in grease making because a smaller quantity of benzoic acid is subsequently needed to complete the in situ reaction which forms the hydroxy aluminum stearate/benzoate soap. Benzoic acid itself is difficult for a grease maker to handle because of its tendency to sublime at temperatures above 100° C.

Greases made with mixed oxyaluminum acylates as provided by the teachings of this invention can be formulated with the various additives heretofore employed in the grease making art, if desired. Thus, for example, a grease of this invention can contain one or more of such additives as rust inhibitors, anticorrosion agents, anti-oxidants, dispersants, fillers, metal deactivators, pressure or anti-wear agents, tackiness agents or systems, and the like, as those skilled in the art will appreciate. Such additives may be added to a grease prior to, during, or after the aluminum soap forming step following the teachings of this invention.

EMBODIMENTS

The present invention is further illustrated by reference to the following Examples. Those skilled in the art will appreciate that other and further embodiments are obvious and within the spirit and scope of this invention from the teachings of these present Examples taken with the accompanying specification.

EXAMPLE 1

To a 3 liter glass resin kettle equipped with a stirring motor and a lid with 3 openings is added the following ingredients: 687.3 grams hydrogenated tallow fatty acids, 503.7 grams benzoic acid, and 673.9 grams isopropyl alcohol. This mixture is heated until it becomes a homogenous clear solution at approximately 60° C. To this mixture is then added 673.9 grams aluminum isopropylate. Heat is then applied to the reaction vessel until it rises to a temperature where isopropyl alcohol begins to distill off. The distillation is continued and periodic temperature readings are taken and the following Table results:

TABLE I

| Time | Pot Temperature | Vapor Temperature |
|---|---|---|
| 0 | 85° C. | 81° C. |
| 1½ hrs. | 85° C. | 81° C. |
| 2 hrs. | 85° C. | 80° C. |
| 3¾ hrs. | 205° C. | 65° C. |

During the above distillation procedure, both the added isopropyl alcohol and the ispropyl alcohol produced by the reaction process are removed from the reaction vessel on a theoretical basis. Heating is continued at 200° C. for 1½ hours and then the reaction mixture is allowed to cool. The product is a light amber clear oily liquid. The aluminum is analyzed to be 5.86% and by further analysis it is determined that the oxyaluminum acylate contained 85% benzoic radicals. The oxyaluminum acylate is dissolved in a mixture of isopropyl benzoate and isopropyl hydrogenated tallowate.

EXAMPLE 2

To 303.7 grams of a grease base oil having the viscosity at 100° F. of 1766 SUS is added 29.8 grams of the compound from Example 1. The resulting mixture is stirred and gradually heated to 90° C. where it is observed that a homogenous, relatively clear mixture results. At this point, there is added to the heated system simultaneously 16.3 grams hydrogenated tallow fatty acid and 0.1 grams benzoic acid with stirring. The amount of ingredients added to the base oil in this grease making Example is calculated in such a manner as to produce a final grease with an aluminum content of 0.5% aluminum metal, a fatty to benzoic ratio of 1.1 to 0.9 and a ratio of 1.92 moles total acids per atom of aluminum. Heating is continued and the temperature is gradually raised to a temperature of 200° C. and the mixture is held at 200° C. for one-half hour. After the acids are added, and as the temperature is thus gradually increased, gradual thickening of the system is observed. The reaction mixture remains clear throughout the heating process and results in a clear grease. No acetic acid odor is detected during this process. After the reaction mixture is held for one-half hour at 200° C., it is allowed to cool and physical properties are determined. The resultant clear grease has a dropping point of 468° F. and an unworked penetration of 307. After working 60 strokes in a standard grease worker, the penetration is 314. The grease remains soft and pliable after standing overnight indicating the absence of false set properties.

EXAMPLE 3

Attempt to Make 85 Mole % Benzoic Mixed Oxyaluminum Acylate Via Acetic Acid Method To a 1000 ml. 3-neck flask is added the following ingredients: 183.2 grams Coray 22 which is lubricating base oil having an approximate viscosity of of 100 SUS at 100° F., 50 grams isopropyl alcohol, 48 grams glacial acetic acid, 33.3 grams hydrogenated tallow fatty acids, and 83.0 grams benzoic acid. The temperature of this mixture is raised to 55° C. at which point 163.4 grams powdered aluminum isopropylate is added to the flask. This mixture is stirred and gradually increased to a point where isopropanol begins to distill off. As the distillation continues, periodic temperature readings are taken and the following Table results:

TABLE II

| Hours | Pot Temperature | Vapor Temperature |
|---|---|---|
| 0 | 89° C. | 81° C. |
| 0.5 | 96° C. | 81° C. |
| 1.0 | 156° C. | 80° C. |
| 1.25 | 198° C. | 81° C. |
| 1.5 | 202° C. | 65° C. |
| 2.0 | 210° C. | 30° C. |
| 2.5 | 194° C. | 30° C. |
| 4.0 | 192° C. | 30° C. |

During this distillation procedure, the material in the flask never goes through a clear state and does not end up clear. It is only thin when the temperature rises to approximately 200° C.; however, it is still an opaque liquid at this point. Very little distillate is taken off between the temperatures of 156° C. and 200° C. indicating that only a small amount of ispropyl acetate ester is formed by this reaction. The total distillate measures 149 grams and accounts for little more than the theoretical ispropanol released by the reaction with the acids plus the 50 grams ispropyl alcohol added to facilitate dispersion of the initial materials.

EXAMPLE 4

The procedure in Example 3 is repeated to make sure that the results are reliable. The same quantities of ingredients are added in the same order and the mixture is stirred and the temperature gradually increased to a point where isopropanol begins to distill off. As the distillation continues temperature readings are taken and the following Table results:

TABLE III

| Hours | Pot Temperature | Vapor Temperature |
|---|---|---|
| 0 | 90° C. | 81° C. |
| .5 | 93° C. | 81° C. |
| 1.0 | 180° C. | 81° C. |
| 1.5 | 200° C. | 35° C. |
| 2.0 | 180° C. | 23° C. |
| 2.5 | 202° C. | 23° C. |
| 3.5 | 196° C. | 23° C. |
| 4.0 | 194° C. | 23° C. |
| 4.5 | 197° C. | 23° C. |
| 5.0 | 197° C. | 23° C. |
| 5.5 | 203° C. | 23° C. |
| 6.0 | 200° C. | 23° C. |

During this experiment extra care is taken to ensure that excessive heat does not damage or interfere with the reaction. At no time does the temperature ever exceed 205° C. As can be seen by the Table, no appreciable isopropyl acetate is taken off as indicated by the low vapor temperatures which are recorded as the pot temperature moves towards 200° C. As with Example 3, the mixture in the flask never turns clear and remains an opaque hetergenous mixture.

EXAMPLE 5

An attempt is made to make a grease from the material produced in Example 4. 302.2 grams of the same grease base oil as employed in Example 2 are placed in a beaker which contains a magnetic stir bar. This beaker is placed on a hot plate and heated with stirring to a temperature of 160° C. 31.4 grams of the product obtained from Example 4 is melted and added to the oil.

During this addition, it is noted that solid particles start forming immediately. The size of the particles are about 1/16th of an inch to ⅛th of an inch in diameter. The mixture is then heated to 200° C. in an attempt to disperse the particles, but this is not successful. The temperature is then lowered to 95° C. at which temperature 16.3 grams hydrogenated tallow fatty acid are added slowly to the mixture under agitation. Then, 0.1 gram benzoic acid is added immediately following this addition of the hydrogenated tallow fatty acids and it is noted that the temperature is 100° C. when the benzoic acid is in. The particles noted above do not disappear. The mixture is then raised again to a temperature of 200° C. The mixture thickens slightly, but still contains the solid opaque particles. This mixture does not appear to be useable as grease because of these opaque particles.

EXAMPLE 6

Preparation of Mixed Oxyaluminum Acylate Containing Benzoic Acid Via the Acetic Acid Method To a 1000 ml. 3-neck flask is added 198.4 grams Coray 22 oil (lubricating base oil having an approximate viscosity of 100 SUS at 100° F.). To this oil in such a flask is added the following ingredients: 50 grams isopropyl alcohol, 48 grams acetic acid, 55.5 grams hydrogenated tallow fatty acids, 73.3 grams benzoic acid. This mixture is warmed slightly to produce a homogenous clear liquid. The temperature is then raised to 65° C. and at this point is added to the system 163.4 grams aluminum ispropylate.

This mixture is stirred and the temperature gradually increased to a point where isopropanol begins to distill off. As the distillation continues periodic temperature readings are taken and the following Table results:

TABLE IV

| Time | Pot Temperature | Vapor Temperature |
|---|---|---|
| 0 | 88° C. | 81° C. |
| .5 | 88° C. | 81° C. |
| 1.0 | 90° C. | 81° C. |
| 1.5 | 99° C. | 81° C. |
| 2.0 | 110° C. | 81° C. |
| 2.5 | 180° C. | 84° C. |
| 3.0 | 200° C. | 87° C. |
| 3.5 | 200° C. | 87° C. |
| 4.0 | 204° C. | 87° C. |

During the distillation a total of 2 moles isopropyl alcohol are removed after which 1 mole of isopropyl acetate is removed all on a theoretical basis. The reaction mixture is thereafter allowed to cool to room temperature. The product is a clear solid amber material having a melting point of approximately 130° C. and by calculation is found to contain 5.44% aluminum indicating a 40.9% solution (in 100 SUS 100° F. lubricating oil) of mixed oxyaluminum stearate/benzoate wherein the mole percent benzoate is 75%.

EXAMPLE 7

Grease Made From Example 6

303.5 Grams of the same grease base oil as employed in Example 2 are placed in a beaker which contains a magnetic stir bar. This beaker is placed on a hot plate and is heated with stirring to a temperature of 160° C. 32.2 grams of the product obtained from Example 10 is melted and added to the oil. Heating is continued with stirring and the temperature is gradually raised to a temperature of 200° C. and it is observed that the mixture is uniformly dispersed. The temperature is then lowered to 95° C. at which temperature 14.5 grams hydrogenated tallow fatty acid are added slowly to the mixture under agitation. Then, 0.9 grams benzoic acid are added immediately following this addition of the hydrogenated tallow fatty acids. The amount of ingredients added to the base oil in this grease making Example is calculated in such a manner as to produce a final grease with an aluminum content of 0.5% aluminum metal, a fatty to benzoic ratio of 1.1 to 0.9 and a ratio of 1.92 moles total acids per atom of aluminum. The mixture is again raised to a temperature of 200° C. and during such period of heating is observed an acid odor resembling acetic acid.

After the acids are added, and as the temperature is thus gradually increased, gradual thickening of the system is observed. The reaction mixture remains clear throughout the heating process and results in a clear grease. After the mixture is held for 15 minutes at 200° C., it is allowed to cool and physical properties are determined. The resultant clear grease has a dropping point of 479° F. and an unworked penetration of 301. After working 60 strokes in a standard grease worker, the penetration is 314.

EXAMPLE 8

To a 22 liter 3-neck flask is added the following ingredients: 4,998.6 grams hydrogenated tallow fatty acid, 2,197.8 grams benzoic acid and 3,816 grams isopropanol. This mixture is heated to approximately 60° C. at which point the mixture is a clear low viscosity homogenous liquid. To this mixture is then added 3,675.6 grams granulated aluminum isopropylate. Heat is applied to the flask and the temperature gradually raised to the point where isopropanol begins to distill off. As the distillation continues temperature readings are taken at 60 minute intervals and the following Table results:

TABLE V

| Pot Temperature | Vapor Temperature |
|---|---|
| 84° C. | 81° C. |
| 85° C. | 81° C. |
| 85° C. | 81° C. |
| 85° C. | 81° C. |
| 93° C. | 81° C. |
| 100° C. | 81° C. |
| 120° C. | 81° C. |
| 166° C. | 84° C. |

At this point, the heating causes the temperature to begin rising much more rapidly and it reaches 200° C. within another hour. During the time of the first and second steps of heating, both the added ispropyl alcohol and 2 moles of produced isopropyl alcohol on a theorectical basis are removed from the flask. The temperature is then maintained at 200° C. for one more hour after which it is allowed to cool. The product is a light amber clear liquid which is analyzed to be 5.67% aluminum and by further analysis it is determined that the oxyaluminum acylate so produced contained 75.3% benzoic radicals. The oxyaluminum acylate so produced contained 75.3% benzoic radicals. The oxyaluminum acylate is dissolved in a mixture of isopropyl benzoate and isopropyl hydrogenated tallowate.

EXAMPLE 9

Grease From Example 8

To 303.8 grams of a grease base oil having the viscosity at 100° F. of 1766 SUS is added 30.8 grams of the compound from Example 8. The resulting mixture is stirred and gradually heated to 90° C. where it is observed that a clear solution results. At this point there is added to the heated system simultaneously 14.3 grams hydrogenated tallow fatty acid and 0.9 grams benzoic acid with stirring. The amount of ingredients added to the base oil in this grease making Example is calculated in such a manner as to produce a final grease with an aluminum content of 0.5% aluminum metal, a fatty to benzoic ratio of 1.1 to 0.9 and a ratio of 1.92 moles total acids per atom of aluminum. Heating is continued and the temperature is gradually raised to a temperature of 200° C. and the mixture is held at 200° C. for one-half hour. After the acids are added, and as the temperature is thus gradually increased, gradual thickening of the system is observed. The reaction mixture remains clear throughout the heating process and results in a clear grease. No acetic acid odor is detected during this process. After the reaction mixture is held for one-half hour at 200° C., it is allowed to cool and physical properties are determined. The resultant clear grease has a dropping point of 509° F. and an unworked penetration of 245. After working 60 strokes in a standard grease worker, the penetration is 286. The grease remains soft and pliable after standing overnight, indicating the absence of false set properties.

I claim:

1. Compounds of the formula

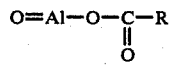

and of the formula

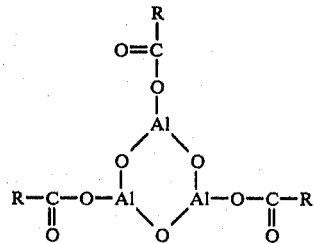

wherein R is selected from the group of radicals consisting of:

Type (A): aliphatic radicals each containing from 10 to 38 carbon atoms, and

Type (B): aromatic radicals each containing from 6 to 16 carbon atoms, and wherein, in any given group of such compounds, the mole percent of said Type (B) radicals ranges from 75 to 95% and the balance up to 100 mole percent thereof is said Type (A) radicals.

2. Compounds of claim 1 wherein said Type (A) radicals are derived from hydrogenated tallow acids and said Type (B) radicals are derived from benzoic acid.

3. Compounds of claim 1 wherein Type (A) radicals are derived from hydrogenated fish oil acids and said Type (B) radicals are derived from benzoic acid.

4. Compounds of claim 1 wherein said Type (A) radicals are derived from stearic acid and said Type (B) radicals are derived from benzoic acid.

5. Compounds of claim 1 wherein said Type (A) radicals are derived from isostearic acid and said Type (B) radicals are derived from benzoic acid.

6. A composition for use in grease manufacture comprising on a 100 weight percent total weight basis
   (a) from about 30 to 70 weight percent of at least one group of compounds of claim 1, and, correspondingly,
   (b) from about 70 to 30 weight percent of an inert organic liquid which has a viscosity of 100° F. ranging from about 35 to 50,000 SUS,
   said component (a) being uniformly dispersed in said component (b).

7. The composition of claim 6 wherein said component (a) is dissolved in said component (b).

8. The composition of claim 6 wherein in said component (a), said Type (A) radicals are derived from stearic acid and said Type (B) radicals are derived from benzoic acid.

9. The composition of claim 6 wherein said Type (A) radicals are derived from hydrogenated tallow acids, and said Type (B) radicals are derived from benzoic acid.

10. The composition of claim 6 wherein said Type (A) radicals are derived from hydrogenated fish oil and said Type (B) radicals are derived from benzoic acid.

11. The composition of claim 6 wherein said Type (A) radicals are derived from isostearic acid, and said Type (B) radicals are derived from benzoic acid.

12. A process for making a grease comprising the steps of
   (A) heating a mixture of petroleum derived hydrocarbon having a viscosity at 100° F. of from about 35 to 50,000 SUS and a composition of claim 6, said mixture containing a total amount of aluminum in the range from about 0.01 to 2.0 weight percent based on total mixture weight, said heating being conducted at temperatures, and for times, sufficient to substantially completely dissolve all starting mixed oxyaluminum acylates present in said hydrocarbon,
   (B) admixing with the resultant such mixture of step (A) a total of from about 0.8 to 1.2 moles based on the total quantity of aluminum present in said resultant such mixture of at least one carboxylic acid material selected from the group consisting of aliphatic monocarboxylic acids containing from 10 through 40 carbon atoms each and aromatic monocarboxylic acids containing from 7 through 28 carbon atoms each, and
   (C) thereafter heating and gradually raising the temperature of the product mixture until at least some of said starting mixed oxyaluminum acylates present in step (A) have been converted into diacyl monohydroxy aluminum soap by reaction in situ with said carboxylic acid material.

13. A grease prepared by the process of claim 12.

14. In an improved process for making a grease from a starting oil having a viscosity at 100° F. of from about 35 to 50,000 SUS by contacting in said oil at least one carboxylic acid material with starting organoaluminum compound, both said carboxylic acid material and said organoaluminum compound being dispersed in said oil, said contacting being carried out at a temperature sufficient to produce reaction between said carboxylic acid material and said organoaluminum compound, said contacting being continued until at least some of said organoaluminum compound has been converted into an aluminum soap and a grease is formed, the improvement which comprises employing as said starting organoaluminum compound at least one compound of claim 1, and wherein said aluminum soap is an aluminum monohydroxy diacylate.

15. The process of claim 14 wherein in said starting organoaluminum compound said Type A radicals are derived from a member of the class consisting of hydrogenated tallow acids and hydrogenated fish oil acids and Type B radicals derived from benzoic acid.

16. The process of claim 14 wherein the total amount of aluminum present is in the range from about 0.01 to 2.0 weight percent based on total weight of said starting oil and said organoaluminum compound.

17. The process of claim 14 wherein said starting organoaluminum compound is initially substantially completely dissolved in said oil before said carboxylic acid material is admixed with said oil.

18. The process of claim 14 wherein said carboxylic acid material is initially substantially completely dissolved in said oil before said starting organoaluminum compound is dispersed in said oil.

19. A grease prepared by the process of claim 14.

20. The process of claim 12 wherein step (A) is practiced before step (B).

21. The process of claim 12 wherein steps (A) and (B) are practiced together.

22. The process of claim 12 wherein step (B) is practiced before step (A).

23. The process of claim 12 wherein said carboxylic acid material so admixed comprises isostearic acid.

24. A grease prepared by the process of claim 23.

25. The compounds of claim 1 wherein said type (B) aromatic radicals are derived from benzoic acid.

* * * * *